(12) United States Patent
Bault

(10) Patent No.: US 6,353,472 B1
(45) Date of Patent: Mar. 5, 2002

(54) DEVICE FOR AUTHENTICATING A PERSON ON THE BASIS OF HIS FINGERPRINTS

(76) Inventor: Richard V. Bault, 45, rue Jacques Verniol, F-95370, Montigny les Cormeilles (FR)

(*) Notice: Subject to any disclaimer, the term of this patent is extended or adjusted under 35 U.S.C. 154(b) by 0 days.

(21) Appl. No.: 09/600,410

(22) PCT Filed: Jan. 15, 1999

(86) PCT No.: PCT/FR99/00064

§ 371 Date: Jul. 17, 2000

§ 102(e) Date: Jul. 17, 2000

(87) PCT Pub. No.: WO99/35964

PCT Pub. Date: Jul. 22, 1999

(30) Foreign Application Priority Data

Jan. 16, 1998 (FR) .............................. 98 00405

(51) Int. Cl.$^7$ .................................................. G06K 9/74
(52) U.S. Cl. ........................................................ 356/71
(58) Field of Search ..................... 356/71; 382/124–127

(56) References Cited

FOREIGN PATENT DOCUMENTS

| FR | 2749955 A1 | 12/1997 |
| GB | 2312040 A | 10/1997 |
| WO | WO 8606266 | 11/1986 |
| WO | WO 8901674 | 2/1989 |
| WO | WO 9425938 | 11/1994 |

Primary Examiner—Frank G. Font
Assistant Examiner—Amanda Merlino
(74) Attorney, Agent, or Firm—Young & Thompson

(57) ABSTRACT

A device for the authentication of a person by his fingerprints prior to an authorization of operations includes a housing having a track for sliding the finger and a sensor having a dimension less than that of the finger, disposed along the track for sliding the finger.

15 Claims, 4 Drawing Sheets

DEVICE FOR AUTHENTICATING A PERSON ON THE BASIS OF HIS FINGERPRINTS

BACKGROUND OF THE INVENTION

The invention relates to a device for the authentication of a person by his fingerprints prior to an authorization for an operation.

DESCRIPTION OF THE RELATED ART

There are known numerous systems of authentication of people based on the comparison of the fingerprints to reference prints or data representative of reference prints memorized for this purpose.

The best known devices are optical devices adapted to sense an image of an entire print, to capture this image to digitize it, and to process the digital data thus obtained for their use and processing by a means adapted to deliver an authorization for an operation. These known optical devices have the drawback of requiring an optical detector surface which is relatively large, greater than or equal to the surface of the fingerprint to be recognized.

There are also known capacitative sensors, such as the sensor sold under the name "Fingertip Sensor" by the German society SIEMENS AG or the sensor sold under the name "FingerLoc" (trademark) by the American company HARRIS SEMICONDUCTOR.

Finally, there is known from FR 2.749.955, a system of reading fingerprints comprising means for reading the fingerprint with a sensor having a relative sliding movement to the finger corresponding to the fingerprint to be analyzed.

This captor comprising an active pyroelectric or piezoelectric layer, has one dimension less than that of the finger corresponding to a fingerprint to be analyzed, whilst its other dimension is greater or equal to that of said finger.

Such a sensor is advantageous because of its reduced dimensions, which permit envisaging its use in portable devices of small size, or its integration into existing devices to fulfill in combination functions in addition to those of this existing device.

SUMMARY OF THE INVENTION

The invention has for its object a device for authenticating a person by his fingerprints prior to the authorization of an operation, of the type comprising a housing having a track for sliding the finger and a sensor with an active pyroelectric or piezoelectric layer having a dimension less than that of a finger, disposed on said sliding track for the finger, in which said sliding track for the finger has a rounded protruding portion and said sensor is disposed adjacent said rounded protruding portion, so as to regularize and optimize taking the digital print from a finger sliding on said sliding track.

According to other characteristics of the invention:

- the device comprises a means for memorizing designs of prints of persons enjoying authorization to perform an operation and a means for comparison of the memorized designs in said memorizing means with a fingerprint taken by the sensor, so as to deliver or not the authorization for an operation;
- the device comprises a hardware support for data containing software adapted to execute a memorization of designs of fingerprints, a modelization of digital takings of fingerprints and a comparison of designs of fingerprints so as to deliver or not an authorization for an operation;
- the device has a configuration of control means for the position of a pointer or a cursor on a computer screen, for example a mouse, a control ball or a pressure tablet;
- the device comprises a memory card reader adapted to receive a design of a fingerprint;
- the device is configured as an electronic payment terminal connected to or comprising a computer unit delivering an authorization for an operation;
- the electronic payment terminal comprises a keyboard or other means for the introduction of values and/or alphanumeric operations;
- the device comprises a memory card reader adapted to receive a design of a fingerprint;
- the device comprises, in combination with the sensor with an active pyroelectric or piezoelectric layer, another means, for example a microphone or a camera, permitting measuring a biometric characteristic other than the fingerprints, to carry out a multi-level biometric verification aiming to increase security, so as to deliver or not an authorization for an operation.

BRIEF DESCRIPTION OF THE DRAWINGS

The invention will be better understood from the description which follows given by way of non-limiting example with reference to the accompanying drawings, in which.

DESCRIPTION OF THE PREFERRED EMBODIMENT

Figure 1:
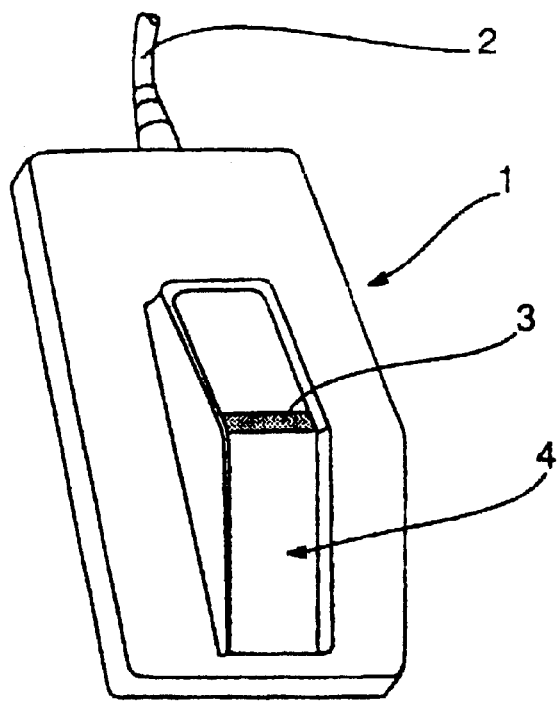
FIG. 1 shows schematically a perspective view of a first embodiment of the invention.

Referring to FIG. 1, a first embodiment of the invention comprises a housing 1 connected by a connection cable 2 to transmit to a computer unit (not shown) data by series transmission, by parallel transmission or with the help of a transmission forming a communication bus, for example a communication bus known by the name USB (Universal Serial Bus).

The plastic housing 1 contains an electronic circuit connected to a fingerprint sensor 3 having a dimension smaller than that of a finger.

The electronic circuit connected to the sensor 3 and contained in the housing 1 preferably comprises a digital analog converter, a clock generator, an amplifier of output level, and an output connector permitting transmission of digital information to the computer unit (not shown).

The electronic circuit preferably comprises a specialized processor associated with a memory constituting a local computer unit.

According to the invention, the sensor 3 is disposed on a track 4 for sliding the finger, for example constituted by a portion in relief relative to the body of the housing 1.

In the illustrated example, the sliding track 4 is shaped as an obtuse dyhedral and the detector 3 is disposed adjacent the summit of the obtuse dyhedral.

Any shape of sliding track, or indication of this sliding track by color marking, is comprised in the present invention, the essential being that the sliding track for the finger has a convexly curved portion, which is to say not hollowed, permitting regularizing and optimizing the taking of the fingerprint of a finger sliding on said sliding track.

Thus it has been determined that the sliding of the finger is more regular and leads to serial reading of fingerprint portions that are usable in the case in which the sliding path has a convexly curved portion, which is to say non-planar.

In this first embodiment of the invention, the housing 1 is connected to a computer unit containing a hardware support for data, for example a hard disc, a diskette, kette a CDROM or equivalent memory means containing software adapted to be used by the computer unit.

Preferably, this software is comprised by a driver for communication with the electronic circuit contained in the housing 1, a software for signature and recognition of fingerprints, a software for managing the print base permitting integration of the preceding software into application software, and permitting communication between the user of the computer unit and the assembly of hardware including the sensor 3. Preferably, the signature and fingerprint recognition software verifies, at the moment of registration of a print, that this print does not already exist in the data base and refuses, at the moment of verification, a mathematical signature comprising solely the elements of the memorized mathematical signature, so as to avoid re-use of a signature that may have been intercepted.

Figure 2:
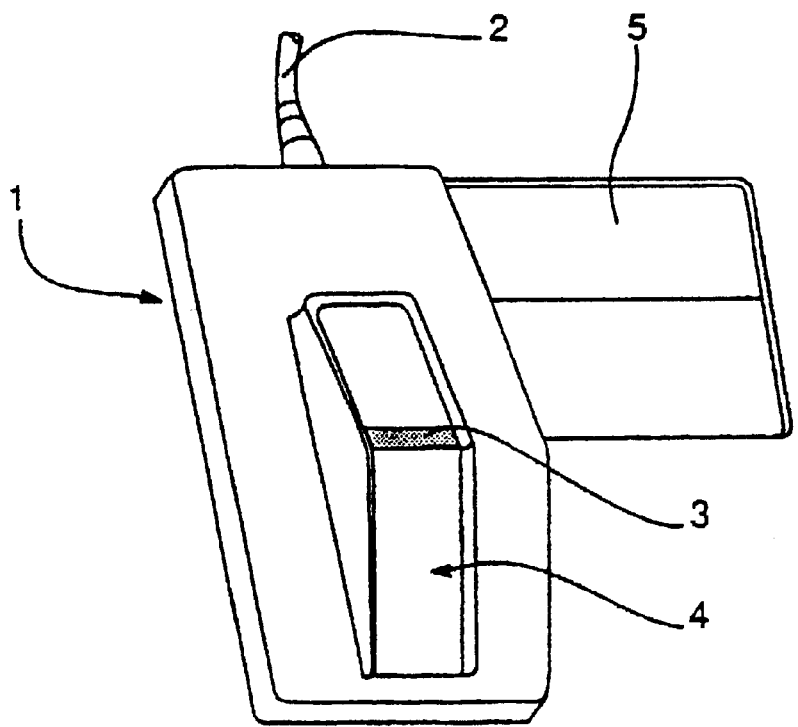
FIG. 2 shows schematically a perspective view of a second embodiment of the invention.

In FIG. 2, the reference numerals identical to those of FIG. 1 relate to elements that are identical or functionally equivalent to the elements of FIG. 1.

This second embodiment of the invention moreover comprises a memory card reader, located in the lower portion of the housing and having a lateral opening parallel to the sliding track 4.

The memory card 5, for example a smart card, constitutes a memory means for designs of fingerprints of a person who enjoys authorization of operation.

The person to be authenticated introduces the memory card 5 into the corresponding reader and carries out the operations of reading the fingerprint by passage of the finger corresponding to the memorized design, along the sliding track 4.

The mentioned software then carries out the comparison of the design or designs memorized in the memory card 5, with the fingerprint taken by the sensor, so as to deliver or not an authorization for an operation.

The invention also covers the modification according to which a hardware support for data contains software for the personalization or encryption of a memory card, so as to personalize the mathematical structure of the design of fingerprints registered by the memory card.

Figures 3, 4:
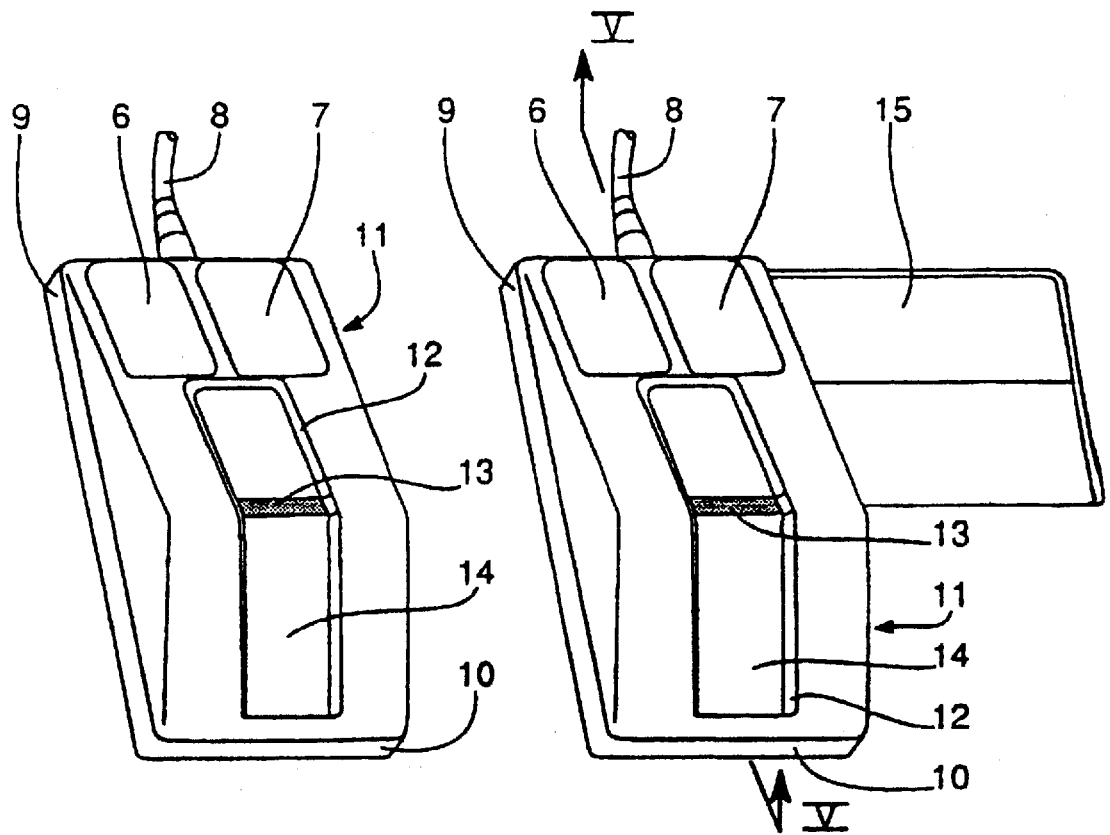
FIG. 3 shows schematically a perspective view of a third embodiment of the invention.
FIG. 4 shows schematically a perspective view of a fourth embodiment of the invention.

In FIG. 3, a housing is configured as a control means for the position of a pointer or a cursor on a computer screen. To this end, the housing has a rolling ball on a slide sheet (not shown) and two control keys 6 and 7 located in the front of the housing. The control buttons 6 and 7 are not limited to any number; additional controls such as a dial or other elements can also be provided without departing from the scope of the present invention.

A cable 8 is provided to connect the device to a computer unit (not shown). An edge having a height sufficient to permit receiving the lower ball and electronic circuit extends peripherally about the device.

The edge 9 has a front portion 10 adapted to be held to avoid displacement of the device during taking fingerprints preliminary to an authorization of an operation.

The external portions of the elements 9 and 10 mentioned above are integrated or of one piece with the assembly 11 constituting the housing, made for example of plastic material.

The housing 11 comprises a mark or an edge 12 delimiting on the one hand in the emplacement of the sensor 13 adjacent a convexly curved portion of a sliding track 14, and surrounding on the other hand the periphery of this sliding track 14.

Figure 5:
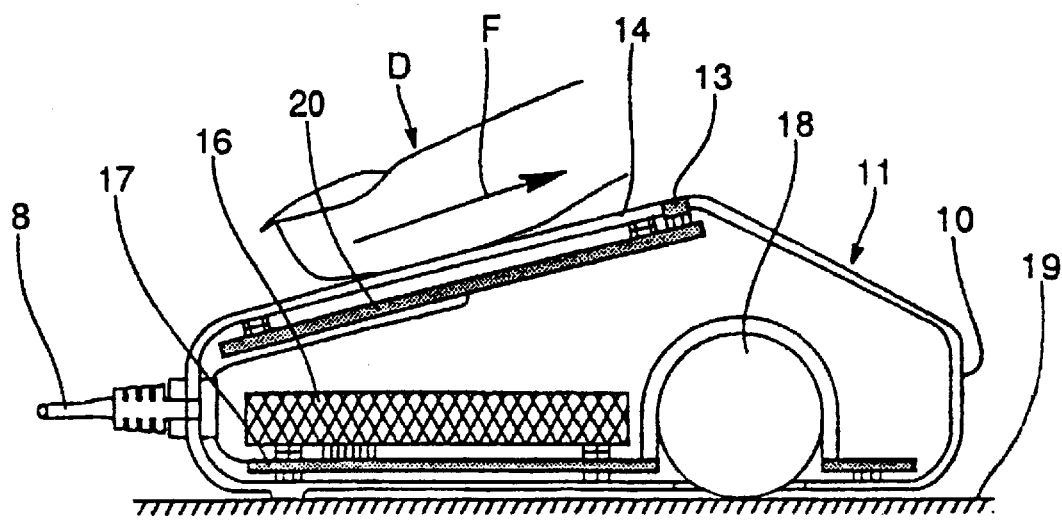
FIG. 5 shows schematically a view in cross-section on a median longitudinal plane on a line V—V of FIG. 4, of a fourth embodiment of the invention.

In FIGS. 4 and 5, identical references to those of FIG. 3 designate elements identical or functionally equivalent to those of FIG. 3.

The device is adapted to receive a memory card 15, for example a smart card adapted to be read by a reader 16 of memory cards, so as to compare a fingerprint read by the sensor 13 to a design of a fingerprint registered in the memory card 15. The device also comprises the electronic circuit 17 associated with the control function of a pointer or a cursor on a computer screen by means of movement of a ball 18 on a surface 19.

The housing 11 finally preferably comprises below the forward portion of the sliding track 14 electronic circuit connected on the one hand to the sensor 13 and on the other hand to a computer unit (not shown) by means of wire connections and the transmission cable 8. The electronic circuit 20 preferably has a specialized processor associated with a memory constituting a local computer unit.

Thus, during movement of a finger D in the direction of the arrow F, the fingerprint ridges are read successively by the sensor 13 and reconstituted by the software contained in the computer unit after having been digitized by the electronic circuit 20.

For this purpose it suffices simply to maintain motionless the surface 10 of the housing 11, for example by holding this surface 10 immovable by blockage against an abutment or with the help of another finger of the person seeking authorization of operation.

Although described with reference to a control mouse of a pointer or a cursor on a data screen, the invention also extends to any control means of the position of a pointer or a cursor on a computer screen comprising a sensor disposed on a sliding track for a finger: a control ball, a pressure tablet, a graphic tablet, a keyboard, a digital keypad, a pointer with a loop and riticule, a pressure stylus, a focal control microphone, a control helmet with perception of movement.

Also, the control member for the position of a pointer or a cursor on a computer screen can be connected by wireless connection, for example by infrared transmission, instead of being connected to the computer unit by means of a cable 8.

The expression "memory card" covers not only smart cards, but also bar code cards, cards with magnetic strips, with magnetic track, cards adapted to be read or written with the help of a laser and cards with two-dimensional code, particularly DATA GLYPH (trademark).

The term "housing" also comprises housings or boxes carrying another means for manually taking alphanumeric data, or housings or boxes comprising a display means, for example liquid crystal.

Figures 6, 7:
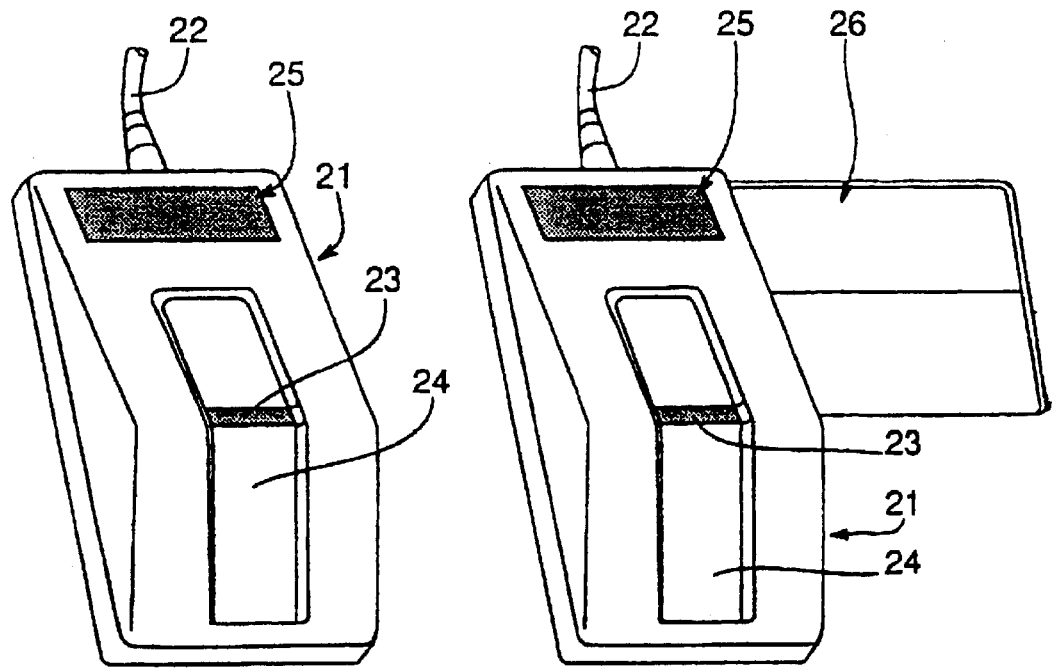
FIG. 6 shows schematically a perspective view of a fifth embodiment of the invention.
FIG. 7 shows schematically a perspective view of a sixth embodiment of the invention.

In FIG. 6, a fifth embodiment of the invention comprises housing 21 connected by a wire connection 22 to a central unit (not shown).

The housing 21 comprises a sensor 23 disposed on a convexly curved sliding track 24, for example in the form of an obtuse dyhedral.

The housing 21 is arranged as an electronic payment terminal adapted to take a fingerprint so as to deliver an authorization for operation of payment. The housing 21 preferably comprises a display means 25 for example of the liquid crystal type, comprising at least one line of alphanumeric character display.

Preferably, the housing 21 comprises a specialized processor with a working memory, a program memory, and if desired a flash memory for managing the digital data base representative of designs of prints as well as the content of a log of transactions of electronic payments made.

The program memory if desired incorporated in the specialized processor can be selected from memories of the PROM or EEPROM type or a telechargeable memory of the FLASH or EEPROM type. This memory constitutes a hardware means for support of the resident software. The resident software comprises an autoverification procedure for the system, an initialization and drive of the sensor 23 of fingerprints, taken of image slices and a reconstruction of the entire image from these slices, an analysis and modeling of this image, a comparison of the image model of a finger with the memorized image design, if desired a local drive of a digital data base representative of designs of prints, and a transaction log.

Preferably, the centralized elements of the software are supported by the memory of the computer unit or of the central server for authorization of payment: thus, the centralized data drive representative of the mathematical models of the memorized fingerprints and the library of primitives usable for the development of application programs, are generally memorized in the central server.

The arrangement of the specialized processor and of the associated electronic circuit in the housing 21 is preferably so as to obtain independent operation of the other peripherals driven by the central server, by using if desired a communication bus of the type USB (Universal Serial Bus).

In FIG. 7, identical reference numerals to those of FIG. 6 show identical or functional equivalents to the elements of FIG. 6.

This sixth embodiment of the invention moreover comprises in combination a reader for a memory card reader 26. The memory card 26 contains in memorized form digital data representative of a design of fingerprints of a person enjoying authorization of operation.

Figures 8, 9:
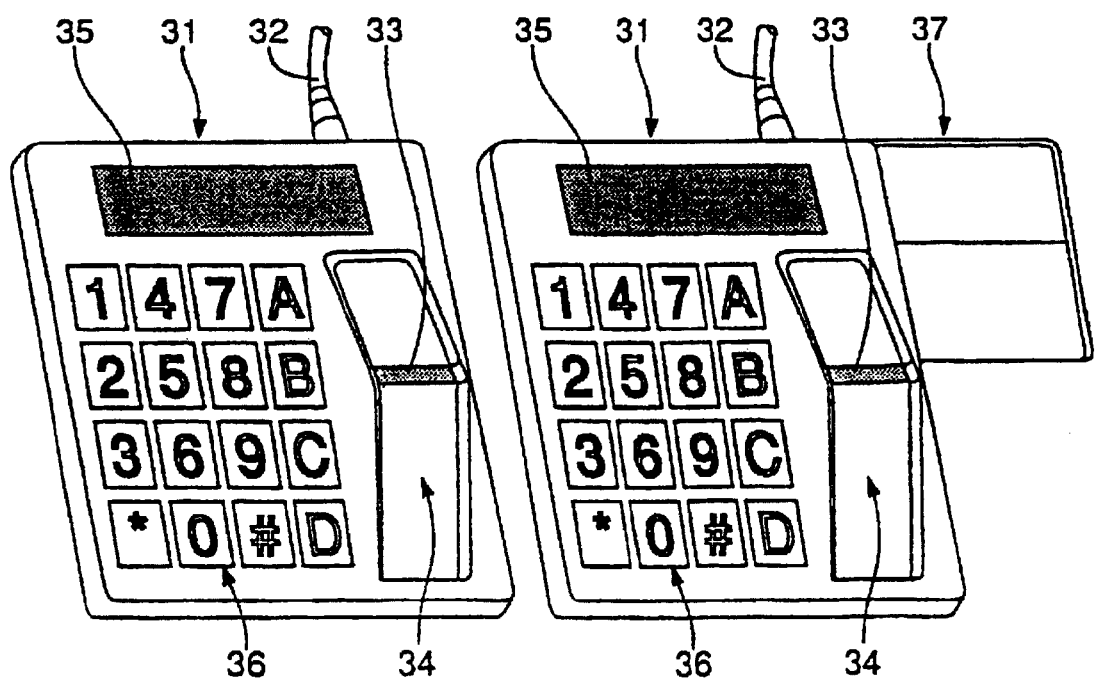
FIG. 8 shows schematically a perspective view of a seventh embodiment of the invention.
FIG. 9 shows schematically a perspective view of an eighth embodiment of the invention.

In FIG. 8, an electronic payment terminal comprises a housing 31 with a wire connection 32 having a sensor 33 of fingerprints disposed on a sliding track 34 for the finger having a convexly curved shape. The housing also has a display 35, for example of the liquid crystal type, and a keyboard 36 or a means for introduction of values or alphanumeric operations. The data introduced with the help of the alphanumeric keys of the keyboard 36 are representative of financial operations or of consultations or of introductions of data giving access to data or to financial operations.

The electronic payment terminal shown in FIG. 9 is functionally equivalent to the terminal of FIG. 8 and moreover comprises in combination a memory card reader. The memory card 37 contains digital data adapted to be used for an identification of a person by means of a fingerprint taken by the sensor 33 and compared to a design of a fingerprint memorized in the memory card 37.

Figure 10:
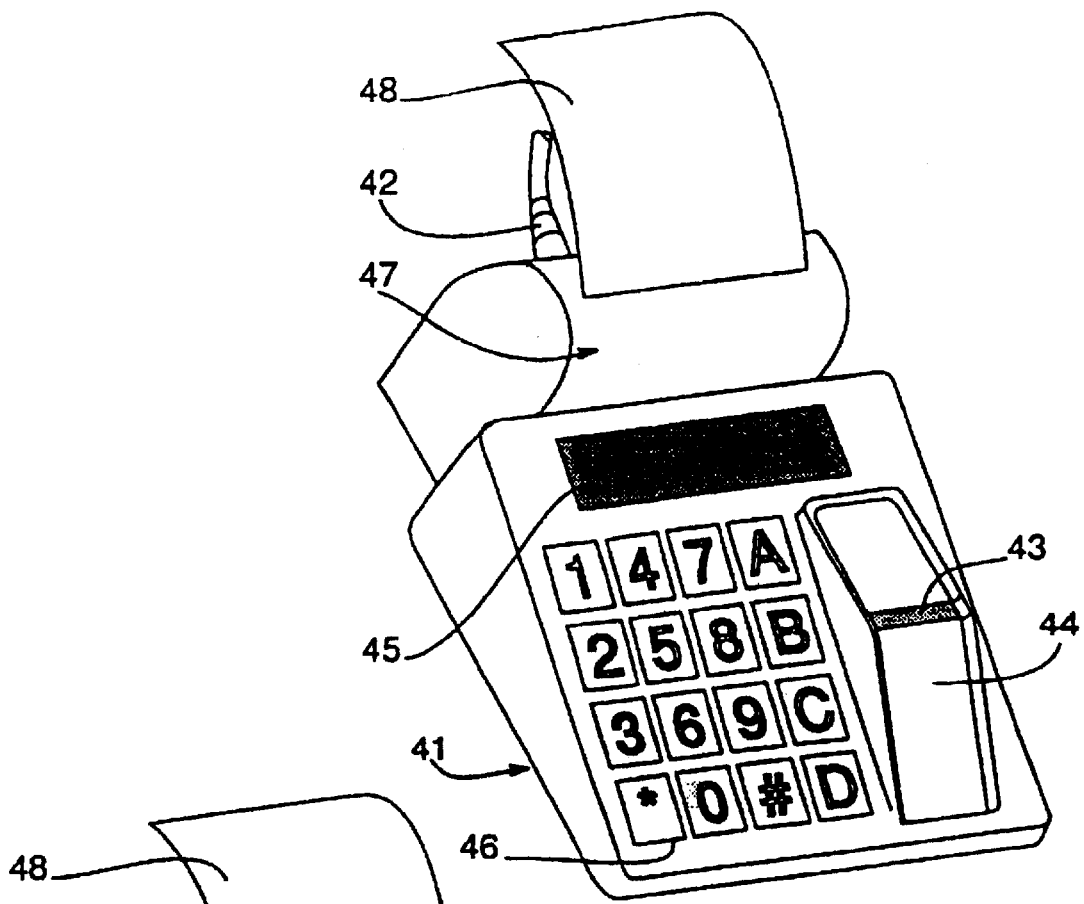
FIG. 10 shows schematically a perspective view of a ninth embodiment of the invention.
Figure 11:
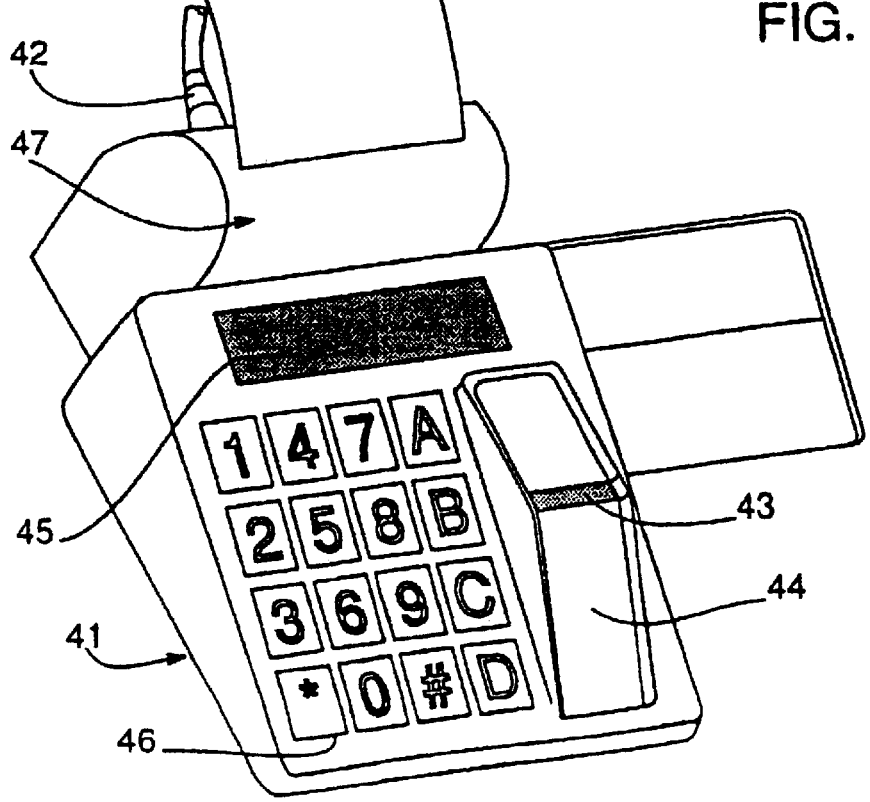
FIG. 11 shows schematically a perspective view of a tenth embodiment of the invention.

In FIG. 10, an electric payment terminal comprises a housing 41 connected by a wire connection 42 to a central unit (not shown), a sensor 43 disposed on a sliding track 44 for a finger, a display 45, an alphanumeric keyboard 46, a printer 47 controlled by the electronic housing 41 and coupled with the latter so as to supply an impression 48 representative of operations or transactions carried out.

Preferably, the impression sheet 48 permits supplying, on demand from the central unit or from an authorized person, a real image of the fingerprint of the person seeking authorization of operation. On the one hand, this fingerprint permits memorizing unauthorized persons having sought without success such authorization, and on the other hand, the real image of this fingerprint is assimilable to a signature in the case of an authorized person who cannot or does not wish to sign, or in the case of important transactions requiring a high level of security as well as incontestable proof of performance.

The invention described with reference to electronic payment terminals also covers as a modification the analogous boxes or housings of larger dimensions, such as boxes or housings for automatic distributors of tickets. In this case, the invention can be used in conjunction with a personal identification number of the type already used for automatic distributors of tickets, so as to provide a supplemental level of security.

Although the embodiments of FIGS. 6 to 11 are described with a wire connection, the invention also covers any modification comprising a wireless connection, for example infrared.

Also, in combination with all the described embodiments of the invention, each device can comprise in combination with the fingerprint sensor, at least one sensor permitting measuring a biometric characteristic other than the fingerprints, to carry out a multi-level biometric verification seeking to increase security, so as to deliver or not an authorization for operations: by way of example, there can be used a microphone to carry out a vocal recognition or a camera to carry out visual recognition of the person seeking an authorization of operations.

There will now be described an example for practice of the invention and its operation such as seen by the user.

The first step of use of the device is the registration of the users. To this end, an authorization for creation of a design is given before the user slides his finger on the sliding track of the sensor so as to take the print of the finger. The fingerprint of the finger is taken by the sensor and reconstituted by the associated electronic circuit and transmitted to a modelization means for taking digital fingerprints. The design created by this modelization means is memorized in a memorization means for designs of finger to prints of persons enjoying an authorization of operation. This memorization can be offshore in a hardware support for data integrated into a computer unit, or local in a specialized memory processor integrated into the housing of the device.

Preferably, an identification code will be attributed to each user which he will use as an access key to his fingerprint design before sliding his finger along the sensor for verification of identity.

The authorization data base will comprise in this case both identification codes and fingerprint designs associated with these identification codes.

After this recordation phase, the user will key in, each time he wishes to obtain authorization of operation, his identification code on the keyboard provided for this and will slide his finger along the fingerprint sensor.

In the case of a computer mouse, the keyboard used to enter the identification code is preferably the keyboard of the computer unit.

In the case of a payment terminal having a keyboard, the keyboard for inputting the identification code is preferably the keyboard of the payment terminal. The same is true for an automatic ticket distributor.

The invention described with reference to particular embodiments is in no way limited, but on the contrary covers all modification of shape and variation of embodiment within the scope and spirit of the invention.

What is claimed is:

1. Device for the authentication of a person by his fingerprints, so as to authenticate said person prior to authorization of operation, of the type comprising a housing (1, 11, 21, 31, 41) carrying a track (4, 14, 24, 34, 44) for sliding a finger and a sensor with an active pyroelectric or piezoelectric layer (3, 13, 23, 33, 43) having one dimension less than that of a finger, disposed on said track (4, 14, 24, 34, 44) for sliding the finger, characterized in that said track (4, 14, 24, 34, 44) for sliding the finger has a protruding portion, and in that said sensor (3, 13, 23, 33, 43) is disposed adjacent said protruding portion, so as to regularize and optimize taking of the fingerprint of a finger sliding on said track (4, 14, 24, 34, 44).

2. Device according to claim 1, characterized in that the device comprises a memorization means for designs of fingerprints of persons enjoying authorization of operation and a means for comparing the designs memorized in said memorization means with a fingerprint taken by the sensor (3, 13, 23, 33, 43), so as to deliver or not an authorization of operation.

3. Device according to claim 2, characterized in that the device comprises a hardware support for data containing software adapted to execute a memorization of designs of fingerprints, a modelization of the digital taking of fingerprints and a comparison of designs of fingerprints so as to deliver or not an authorization of operation.

4. Device according to claim 2, characterized in that the device moreover comprises a means or a software adapted to carry out a modelization of a fingerprint so as to memorize the design of the fingerprint.

5. Device for controlling the position of a pointer or a cursor on a computer screen, comprising a device according to claim 1.

6. Device according to claim 1, characterized in that the device comprises a memory card reader (5, 15, 26) adapted to receive a design of a fingerprint.

7. Device according to claim 1, characterized in that the device moreover comprises an electronic payment terminal (21, 31, 41) comprising a computer unit delivering an authorization of operation.

8. Device according to claim 7, characterized in that the electronic payment terminal comprises a keyboard (36, 46) or other means for introduction of values and/or alphanumeric operations.

9. Device according to claim 7, characterized in that the device comprises a memory card reader (26, 37) adapted to receive a design of a fingerprint.

10. Device according to claim 1, characterized in that the device comprise moreover an electronic payment terminal, which is connected to an independent computer unit delivering an authorization of operation.

11. Device according to claim 1, characterized in that the device comprises, in combination with the sensor with an active pyroelectric or piezoelectric layer, another means, for example a microphone or a camera, permitting measuring a biometric characteristic other than fingerprints, to carry out a multi-level biometric verification seeking to increase security, so as to deliver or not an authorization of operation.

12. Device according to claim 3, characterized in that the device moreover comprises a means or a software adapted to carry out a modelization of a fingerprint so as to memorize the design of the fingerprint.

13. Device according to claim 8, characterized in that the device comprises a memory card reader (26, 37) adapted to receive a design of a fingerprint.

14. A device for the authentication of a person by the person's fingerprints, comprising:

a housing (1, 11, 21, 31, 41);

a track (4, 14, 24, 34, 44) carried on the housing, the track providing a path for sliding a finger, the track having a protruding portion; and a sensor with an active pyroelectric or piezoelectric layer (3, 13, 23, 33, 43) having one dimension less than that of a finger, disposed on the protruding portion of the track (4, 14, 24, 34, 44), the sensor (3, 13, 23, 33, 43) being disposed adjacent the protruding portion of the track so as to regularize and optimize taking of the fingerprint of a finger sliding on the track (4, 14, 24, 34, 44).

15. A device for the authentication of a person by the person's fingerprints, comprising:

a housing with an upper surface;

a track mounted on the upper surface, the track including a path for sliding a finger, the track having a protruding portion extending above the upper surface; and a sensor with an active pyroelectric or piezoelectric layer having one dimension less than that of a finger, disposed on the protruding portion of the track, the sensor being disposed within the track so as to regularize and optimize taking of the fingerprint of a finger sliding on the track.

* * * * *